United States Patent [19]

Henslee et al.

[11] Patent Number: 5,051,354

[45] Date of Patent: Sep. 24, 1991

[54] DETECTION OF ALTERED IGA1 IN FLUID SAMPLES

[75] Inventors: Jerry G. Henslee; G. Michael Hass, both of Libertyville; Jay R. Schenck, Waukegan; Harry G. Rittenhouse, Lake Bluff, all of Ill.

[73] Assignee: Abbott Laboratories, Abbott Park, Ill.

[21] Appl. No.: 181,892

[22] Filed: Apr. 15, 1988

[51] Int. Cl.$^5$ ................. G01N 33/566; G01N 33/574
[52] U.S. Cl. ...................................... 435/7.8; 435/28; 435/810; 435/7.92; 435/7.94; 436/501; 436/513; 436/518; 436/534; 436/813; 436/827
[58] Field of Search .......................... 435/7, 28, 810; 436/501, 513, 518, 534, 813, 827

[56] References Cited

U.S. PATENT DOCUMENTS

| | | | |
|---|---|---|---|
| 4,389,392 | 7/1983 | Adachi | 436/64 |
| 4,571,382 | 2/1986 | Adachi | 435/7 |

FOREIGN PATENT DOCUMENTS

| | | |
|---|---|---|
| 0043359 | 6/1981 | European Pat. Off. |
| WO87/00289 | 1/1987 | PCT Int'l Appl. |

OTHER PUBLICATIONS

Stockert et al. *Proc. Natl. Acad. Sci. USA,* 79. 6229–6231, 1982.
Henslee et al., *Biol. Abs.,* 87, Abs. No. 39400, 1989.
Dawson et al., *Biochem. Jour.,* 107, 341–352, 1968.
Pierce-Cretel et al., *European Jour. Biochem.,* 114, 169–178, 1981.
Cretel et al., in Shaver et al. (EDS), Proceedings 5th International Symposium Glycoconjugates, Kiel, 1979, pp. 26–27.
LoGerfo et al., (1976) *J. Surg. Res.* 20:481.
Homburger et al., (1984) *A.J.C.P.* 81:569.
Kvale et al., (1987) *Cancer* 59:203.
Watanabe et al., (1983) *Otolaryngol Head Neck Surg.* 91:136.
Pekelharing et al., (1987) *Anal. Bio.* 165:320.
J. Henslee et al., *Journal of Clinical Laboratory Analysis,* vol. 2, 1988, pp. 225–234.
J. Baenziger et al., *Journal of Biological Chemistry,* vol. 249, No. 22, 25th Nov. 1974, pp. 7270–7281.
M. E. Conley et al., *Molecular Immunology,* vol. 20, No. 9, 1983, pp. 977–981.

*Primary Examiner*—David A. Saunders
*Attorney, Agent, or Firm*—Daniel R. Curry; Priscilla E. Porembski

[57] ABSTRACT

The invention is a novel immunoassay method for detection of the immunoglobulin IgA$_1$ with O-linked oligosaccharides lacking sialic acid in fluid samples, such as blood, serum and plasma. Particularly, the invention is an immunoassay method which extracts total IgA from fluid samples by reaction with an immobilized anti-IgA antibody, and then detects only the IgA$_1$ fraction with labeled peanut agglutinin.

15 Claims, 3 Drawing Sheets

DETECTION OF ALTERED IGA1 IN FLUID SAMPLES

FIELD OF THE INVENTION

This invention relates to a novel immunoassay method for the detection of immunoglobulin IgA$_1$ with altered carbohydrate moieties in biological fluids. Particularly, the invention is an immunoassay method for detecting IgA$_1$ immunoglobulin by extracting total IgA from body fluids by reaction with an immobilized anti-IgA antibody and then detecting the IgA$_1$ containing galactose Beta 1-3-N-acetylgalactosamine-protein using labeled lectin.

BACKGROUND OF THE INVENTION

Tumor markers are continually being sought to aid in both the monitoring of and the in-vitro diagnosis of cancer, as is well known in the art. For example, commercial assays, such as the carcinoembryonic antigen and alpha-fetoprotein immunoassays, are available to detect the presence of certain tumor markers in biological fluids.

Serum secretory IgA(SIgA) has been reported in the literature as a tumor marker for various carcinomas. Some researchers report that assays for total SIgA are too non-specific for cancer and of no value for cancer detection, LoGerfo, P. et al., (1976) J. Surg. Res., 20:481. Other researchers showed that the measurement of total SIgA could be of value diagnostically in certain instances of carcinomas and chronic liver disease, Homburger, H. A., et al., (1984) A.J.C.P. 81:569; Kvale, D. et al., (1987) Cancer 59:203; Watanabe, T. et al., (1983) Otolaryngol Head Neck Surg 91:136. As a result, immunoglobulins or other glycoproteins that may be associated with cancer and other disease states, especially chronic hepatic disease, have been investigated for use in diagnostic assays.

No single tumor marker currently available for testing can detect all carcinomas or pre-cancerous stages of a potential carcinoma. Therefore, a number of assays may be used to diagnose and monitor these disease states in order to improve the accuracy of the diagnosis. One problem is that some tumor markers may not be detected because current assays are not sensitive or specific enough to do so and important diagnostic information is never obtained.

Another problem associated with producing a specific and sensitive immunoassay is that repeated attempts to develop antibodies to a very specific antigen can be unsuccessful, thereby making an immunoassay to a specific antigen impossible. Also, the production of antibodies, when possible, is an elaborate and expensive process. The ability of a naturally occurring substance to replace antibodies in an assay would be beneficial.

In order to avoid using antibodies either partially or totally in an assay, and because they posses certain binding affinities, lectins have been employed in various assays. Lectins can recognize and bind to particular carbohydrate structures on the oligosaccharide moieties of glycoproteins. For instance, U.S. Pat. Nos. 4,389,392 and 4,571,382 to Adachi describe methods of using lectins which bind to glycoproteins with a terminal galactose (Beta 1-3 or Beta 1-4)-N-acetylglucosamine or terminal galactose (Beta 1-3 or Beta 1-4)-N-acetylgalactosamine in order to detect tumor associated glycolinkage containing substances. However, the methods described in these patents fail to use any immunological means to first specify which molecules are to be assayed, thereby losing a large measure of specificity.

PCT Application No. WO 87/00289 discloses a test method in which lectins are used to form complexes with soluble desialylated glycoproteins which are then contacted with a detecting antibody. A variant of the test method is disclosed where the desialylated glycoprotein forms a complex with a specific antibody and the labeled lectin is then contacted with the complex. In both cases, the antibody must be specific to the desialylated glycoprotein in order to selectively bind to the glycoprotein. Although the lectin is specific to a particular binding site on the oligosaccharide moiety of the desialylated glycoprotein, a substantial portion of the specificity of the test lies with the ability of the antibody to bind to the correct antigen.

In EPO Patent Application 0 043 359 a test method is described in which a solid phase coated with an antibody specific to the glycoprotein to be analyzed is contacted with a sample to form a complex, to which the labeled lectin is added. Again, the antibody must be specific to the glycoprotein. A similar assay configuration is described by Pekelharing, J. M., et al., (1987) Anal. Bio. 165:320.

The oligosaccharide moieties of glycoproteins are attached to the protein moiety by O-glycosidic or N-glycosidic bonds. Carbohydrate structures of glycoprotein oligosaccharides synthesized by tumor cells are often different from the carbohydrate structures in the normal cell counterpart, thereby making such glycoproteins potential tumor markers. Many of these tumor markers have been identified as mucin glycoproteins. Mucins are high molecular weight glycoproteins characterized by unusually high carbohydrate content and carbohydrate side chains that are linked by O-glycosidic bonds to the protein chains. IgA$_1$, but not IgA$_2$, also contains carbohydrate side chains that are linked to the protein chain by O-glycosidic bonds. The O-linkage occurs between the hydroxyl groups of serine or threonine of the polypeptide and the reducing ends of N-acetylgalactosamine of the oligosaccharide. Certain lectins recognize and bind to the D galactose Beta (1-3)-N-acetylgalactosamine (DGalBeta(1 3)DGalNAc) oligosaccharide structure O-linked to the polypeptide chains of IgA$_1$ and mucin.

Mucins and IgA$_1$ are the major glycoproteins in serum and body fluids with this O-linkage; the vast majority of serum glycoproteins have N-glycosidic linkages. These N-linkages occur between the amide nitrogen of asparagine and the reducing end of N-acetylglucosamine.

Oligosaccharide moieties of O-linked glycoproteins may be altered in cancer patients due to tumor cell necrosis and the release of glycosyltransferases and glycosidases in the vicinity of tumors. The glycoproteins IgA$_1$ and mucin contain O-linked oligosaccharides and can serve as substrates for the released glycosyltransferases and glycosidases. When glycosidases and glycosyltransferases are released from tumors, the O-linked carbohydrate structure of the IgA$_1$ molecule may be altered.

Unaltered IgA$_1$ does contain DGalBeta(1-3)DGalNAc structures accessible to lectin binding, resulting in low levels or background normal levels of these O-linked carbohydrate side chains. However, when the IgA$_1$ molecule is altered by glycosidases the number of these DGalBeta(1-3)DGalNAc structures accessible to lectin binding increases.

It would be advantageous to be able to detect these cancer-altered $IgA_1$ immunoglobulins or to detect a change in the proportion of $IgA_1$ to $IgA_2$ by measuring the O-linked carbohydrate side chains on the $IgA_1$ molecules with a high level of specificity. Particularly advantageous would be an immunoassay method that uses lectins and not an antibody to detect these side chains.

SUMMARY OF THE INVENTION

The present invention is a novel immunoassay method for determining the presence or amount of altered $IgA_1$ immunoglobulin in various body fluids, such as serum, plasma, sputum, urine and feces. The term "altered $IgA_1$" shall include all $IgA_1$ with O-linked oligosaccharides and shall include both normal, non-altered $IgA_1$ and $IgA_1$ that has been affected by disease states, such as tumors. The method comprises contacting the sample with an anti-IgA antibody, forming an anti-IgA/IgA complex, then contacting this complex with a labeled lectin that can bind to DGalBeta(1-3)DGalNAc $IgA_1$ but not the sialylated $IgA_1$ or $IgA_2$ which lacks the O-linked oligosaccharides, thereby forming an anti-IgA/$IgA_1$/lectin complex. The presence or amount of the bound or unbound label measures the presence or amount of the altered $IgA_1$ in the sample. The label may be any label capable of producing a detectable signal, such as, for example, an enzyme, a radioisotope or a fluorescent molecule.

This invention also contemplates an in-vitro diagnostic kit to determine the presence or amount of altered $IgA_1$ in a fluid sample which consists of polystyrene beads coated with anti human IgA antibodies, a labeled lectin which has specificity for said altered $IgA_1$ and not $IgA_2$, specimen dilution buffer and colostrum IgA standards.

Altered $IgA_1$, particularly in serum and plasma, has been shown in our studies to be elevated over a normal population in patients with cancer of the lungs, colon, head and neck, breast, kidney, bladder, prostate and pancreas and also in certain nonmalignant disease states, such as ulcerative colitis, colonic polyps and pancreatitis. When the results from the present invention are compared to those of the carcinoembryonic antigen (CEA) immunoassay, one of the most widely used tests for a serological marker in colorectal cancer patients, an additive effect is seen when both tests are used together. Thus, the altered $IgA_1$ assay in combination with the CEA assay provides more clinical information than does CEA alone.

DETAILED DESCRIPTION OF THE INVENTION

Figure 1:
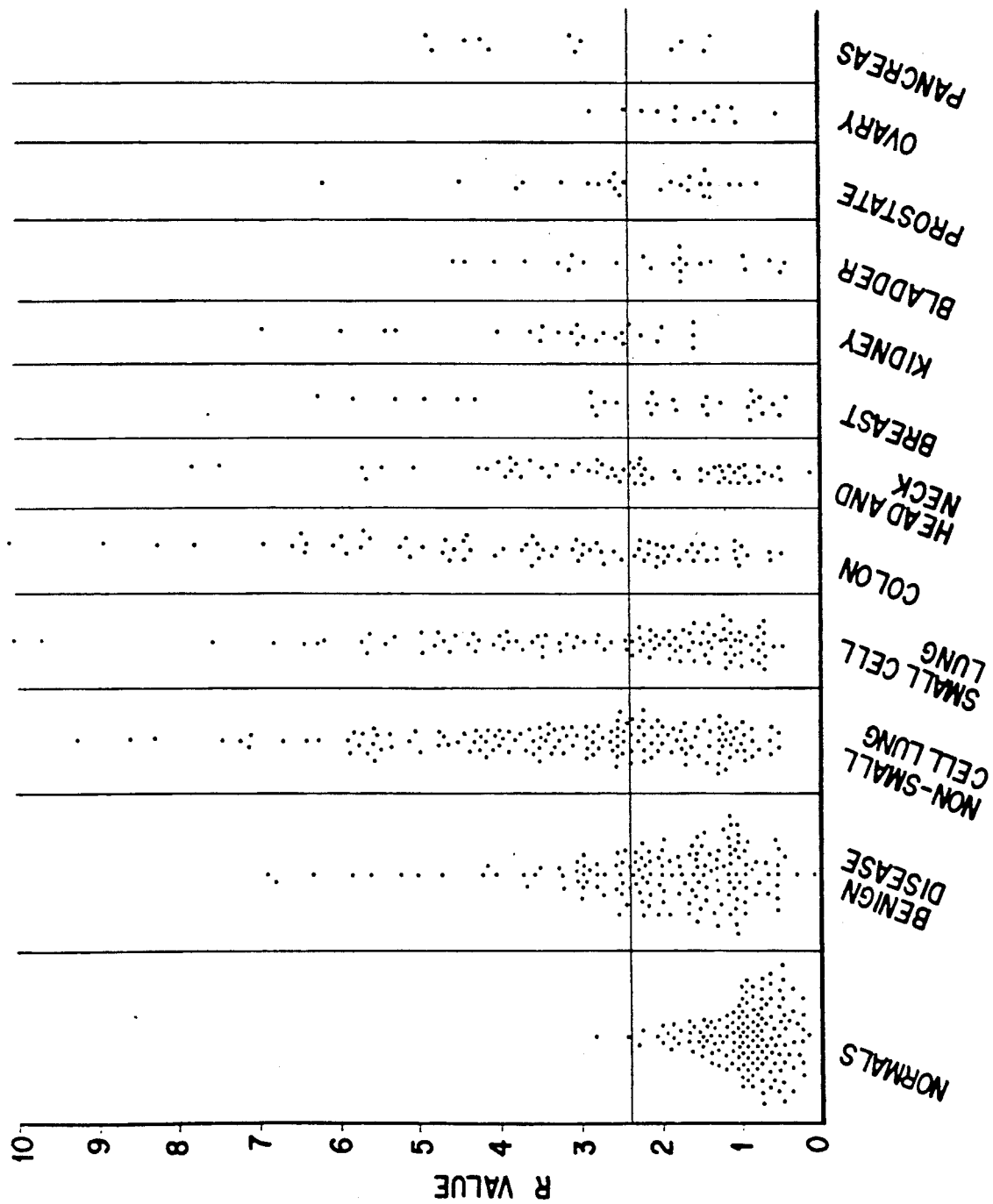
FIG. 1 shows results from a panel of 845 serum specimens as tested using the anti-IgA-peanut agglutinin enzyme immunoassay of Example 1.

The present invention provides a method for determining the presence or amount of $IgA_1$ with altered O-linked oligosaccharides in a fluid sample comprising:

a) contacting the fluid sample with an anti-IgA antibody bound to a solid phase to form an anti-IgA/IgA solid phase complex; and b) contacting the anti-IgA/IgA solid phase complex with a labeled lectin with specificity for said $IgA_1$ to form an anti-IgA/$IgA_1$/lectin solid phase complex when altered $IgA_1$ is present in the fluid sample; and c) determining the presence or amount of label bound or unbound to the anti-IgA/$IgA_1$/lectin solid phase complex as a measure of the presence or amount of said $IgA_1$ in said fluid sample.

The specificity of this anti-IgA immunoassay is directed by both the antibody and the lectin.

The fluid samples assayed in this new immunoassay may be any fluid sample, but will normally be a body fluid, such as blood, serum, plasma, sputum, urine or feces, most preferably being blood, serum or plasma.

The anti-IgA antibody may be a polyclonal or monoclonal antibody specific for IgA or $IgA_1$ and is adsorbed or covalently bound to a solid phase, such as polystyrene beads, microparticles, wells, strips, plates or other suitable solid supports which are well known to those skilled in the art.

Lectins useful in the practice of the invention include any lectins which recognize and bind to the DGalBeta(1-3)DGalNAc oligosaccharide structure O-linked to the polypeptide chain of $IgA_1$ and mucin. Presently particularly preferred lectins for this purpose include peanut agglutinin (PNA) and Bauhinia purpurea alba agglutinin (BPA), although other lectins having the appropriate specificity may be employed.

The label used may be an enzyme, a radioisotope, a fluorescent label or any other chemical or biological entity which will produce a detectable signal and is well known to those skilled in the art. If an enzyme is used as the label, the substrate forms a colored product in the presence of the enzyme. For example, if horseradish peroxidase is used, o-phenylenediamine is added as a substrate to form a colored product which can be measured spectrophotometrically.

If a radioisotope is used as the label, no substrate is needed to activate the label, and after the appropriate amount of incubation of the radiolabeled lectin and the solid phase, unbound radiolabeled lectin is removed by washing, and bound radiolabeled lectin is determined by measuring radioisotope bound to the solid phase.

Preferably, the label on the lectin is an enzyme, such as alkaline phosphatase, B galactosidase, and glucose oxidase. Most preferably the label used with the lectin is horseradish peroxidase enzyme.

In the enzyme immunoassay configuration of this new assay, the fluid sample is added to the anti-IgA antibody and incubated. Total IgA, consisting of both the $IgA_1$ and $IgA_2$ fractions, is now bound to the anti-IgA antibody. Any IgA in the sample that is not bound to the anti-IgA antibody and any residual sample components are then removed by wasting. Next, the enzyme labeled lectin, which has specificity for the DGalBeta(1-3)DGalNAc receptors on the extracted $IgA_1$, is added to the washed beads. The beads containing bound sample IgA and the labeled lectin are incubated. After an appropriate length of time, the beads are again washed and then transferred to reaction tubes, where a substrate is added. The reaction tubes are then incubated. The reaction is quenched and the label is detected in the solid phase as a measure of the lectin binding sites associated with the $IgA_1$ in the sample.

The following examples illustrate the present invention.

EXAMPLE 1

This example describes an assay to determine the presence or amount of $IgA_1$ with altered carbohydrate moieties in serum, using an enzyme labeled lectin.

A. Preparation of Polyclonal Antibodies to IgA

The polyclonal antibody used to bind $IgA_1$ was prepared from rabbit antisera to human IgA (alpha chain), obtained from ICN ImmunoBiologicals (catalogue #65-065). This antibody was prepared in the following manner: the IgG fraction was purified from the antisera by conventional protein A affinity chromatography. Antisera was applied to a protein A affinity column equilibrated in 20 mM Tris—HCl, 0.2 M NaCl, pH 8.3. The column is eluted with the same buffer while collecting fractions. Elution was continued until absorbance at 280 nm returned to baseline The column was then eluted with 0.1 M glycine-HCl, pH 3.0, collecting fractions until the 280 nm absorbance returned to baseline. Fractions containing protein as determined by 280 nm absorbance were pooled from the pH 3.0 elution step and dialyzed against 10 mM sodium phosphate, pH 7.5. The dialyzed antibody was used to coat the polystyrene beads. The antibody is monospecific against human IgA (alpha chains) and not specific against heavy chains of human IgG and the heavy chains of IgM.

It is believed that any antibody having a specificity for the alpha chain portion of IgA will work as will. The rabbit antihuman IgA antibody was used as the antibody for the anti-IgA PNA enzyme immunoassay.

B. Preparation of PNA Lectin Horseradish Conjugate

To prepare the PNA, 250 g of raw peanuts were ground in 250 ml of distilled water with a Waring blender for 3 minutes at room temperature, and the homogenate was stirred with 3 liters of acetone at 4 degree C. overnight and was then suction filtered The residue was air dried and 200 g of the residue was suspended in 1150 ml of 0.15 M NaCl, which was stirred at room temperature for one hour and centrifuged at 10,400×g for one hour. The supernatant was adjusted to 75% saturation ammonium sulfate, the pH adjusted to 5.5, and the mixture stirred overnight at 4 degrees C. The mixture was then centrifuged and the pellets dissolved in distilled water and dialyzed against water extensively, and then dialyzed against phosphate buffered saline (PBS). The dialyzed fraction was applied to a column of Sepharose 6B which had been acid treated and equilabrated in PBS. The column was eluted with PBS until 280 nm baseline absorbance was reached. The column was eluted with PBS containing 0.4 M D-galactose and the fractions demonstrating 280 nm absorbance were pooled and exhaustively dialyzed against (PBS). The dialyzed pool was purified PNA.

Horseradish peroxidase (HRPO) was purchased from Sigma Chemical Co., and was conjugated to PNA by the following method:

To HRPO at 15 mg/ml in 1 mM sodium acetate, pH 4.5, was added sodium metaperiodate at a final concentration of 33 mM and the mixture was incubated 15 minutes at room temperature. The mixture was passed through a Sepharose G-25 column equilibrated in the acetate buffer and the brown and that was collected was activated HRPO. Activated HRPO at 1 mg/ml final concentration was added to PNA at 4 mg/ml (final concentration) in 50 mM bicarbonate pH 9.5 and incubated for 4 hours at room temperature. The reaction was quenched by adding sodium borohydride to a final concentration of 2.6 mM and allowing this to react 30 minutes at 4 degrees C. Acetone was added to a final concentration of 0.2% v/v to quench the sodium borohydride reaction.

C. Anti-IgA PNA Enzyme Immunoassay Procedure

Polystyrene beads, 0.25 inch in diameter, were coated by passive absorption with 10 micrograms/ml rabbit antihuman IgA at room temperature overnight. 25 microliters of serum specimen or colostrum IgA standard (Sigma Chemical Co., catalogue # I 0633), 200 microliters of assay diluent (0.1%BSA and 0.02% Tween 20 in 10 mM sodium phosphate, 150 mM NaCl, pH 7.2), and a coated bead were added to wells of a plastic reaction tray (Abbott Laboratories, list #4046-16).

Standards were prepared as 5, 20, 60 and 150 micrograms/ml of colostrum IgA diluted in a pool of normal human sera. This normal human sera pool was also tested as a reference control, and a panel of 845 serum specimens were the test samples.

The tray was incubated at 37 degrees C. for one hour. The beads were washed with distilled water and then incubated again at room temperature for two hours with 200 microliters of HRPO conjugated PNA diluted in assay diluent. The beads were washed with distilled water after this incubation and then transferred to reaction tubes. A 0.3 ml aliquot of o-phenylenediamine substrate (obtained from Abbot Laboratories OPD reagent kit, list #6172-30) was added to each reaction tube, which was then incubated for thirty minutes at room temperature. To quench the peroxidase reaction 1.0 ml of 1N sulfuric acid was added to each tube and the absorbance was measured at 492 nm with a spectrophotometer. The final result (R value) for each standard and specimen was reported as a ratio with respect to the reference control assay value.

FIG. 1 represents the results from the panel of 845 serum specimens. The mean R value of the normal specimens was 0.98±0.47 S.D. which was used to establish three cutoff R values, which are, 1.91 (mean plus two S.D.), 2.38 (mean plus three S.D.) and 3.0. At the R values of 1.91 and 2.38, 5.1% and 1.2% respectively of normal specimens were greater than the R values; at the 3.0 value, 0% of normal specimens were elevated.

The R values from all 845 serum specimens were analyzed with respect to these R values, as shown in Table I. The highest specificity was achieved with the 3.0 R value where all normal specimens were negative, 13% of the benign disease specimens were above the R value, and over 40% of the specimens for four different types of cancer were elevated. As the cutoff R value was lowered, the sensitivity of the assay for detecting the cancer specimens increased, but there was poorer specificity due to an increased number of elevated benign disease specimens.

TABLE I

SUMMARY OF ANTI-IgA - PNA EIA
WITH MALIGNANT DISEASES AND CONTROLS

| Cutoff R Value | Percent of Patient Serum Specimens Above Cutoff | | | N |
|---|---|---|---|---|
| | 1.91 | 2.38 | 3.0 | |
| Normals | 5 | 1 | 0 | 158 |
| All benign diseases | 43 | 26 | 13 | 163 |
| Malignancies | 63 | 50 | 37 | 559 |
| Lung | 64 | 52 | 40 | 285 |

TABLE I-continued
SUMMARY OF ANTI-IgA - PNA EIA WITH MALIGNANT DISEASES AND CONTROLS

| Cutoff R Value | Percent of Patient Serum Specimens Above Cutoff | | | N |
|---|---|---|---|---|
| | 1.91 | 2.38 | 3.0 | |
| Colon | 73 | 60 | 49 | 83 |
| Head & Neck | 62 | 43 | 30 | 63 |
| Breast | 48 | 35 | 19 | 31 |
| Kidney | 84 | 64 | 40 | 25 |
| Bladder | 46 | 38 | 29 | 24 |
| Prostate | 52 | 43 | 22 | 23 |
| Ovarian | 31 | 8 | 0 | 13 |
| Pancreatic | 67 | 67 | 42 | 12 |

Table II is a summary of the results of the benign diseases. At the 1.91 R value, all nine pulmonary specimens were elevated above the cutoff, whereas only two were so elevated above the 3.0 cutoff. Seven of eight of the bowel benign specimens were above the 1.91 cutoff, but only one was elevated above the 3.0 cutoff. The specimens from patients with diabetes had 30% of the specimens elevated above the 3.0 cutoff.

TABLE II
SUMMARY OF ANTI-IgA - PNA EIA WITH BENIGN DISEASES

| Cutoff R Value | Percent of Patient Serum Specimens Above Cutoff | | | N |
|---|---|---|---|---|
| | 1.91 | 2.38 | 3.0 | |
| All benign diseases | 43 | 26 | 13 | 163 |
| Lung | 100 | 78 | 22 | 9 |
| Colon | 88 | 38 | 13 | 8 |
| Benign prostatic hyperplasia | 44 | 24 | 12 | 75 |
| Prostatitis | 21 | 0 | 0 | 19 |
| Diabetes | 40 | 30 | 30 | 20 |
| Polycythemia | 35 | 23 | 6 | 17 |
| Other | 30 | 30 | 10 | 10 |

These examples demonstrate that serum IgA in cancer patients and in some benign diseases is often different from the serum IgA in normal subjects with respect to oligosaccharide chains linked to $IgA_1$.

Figure 2:
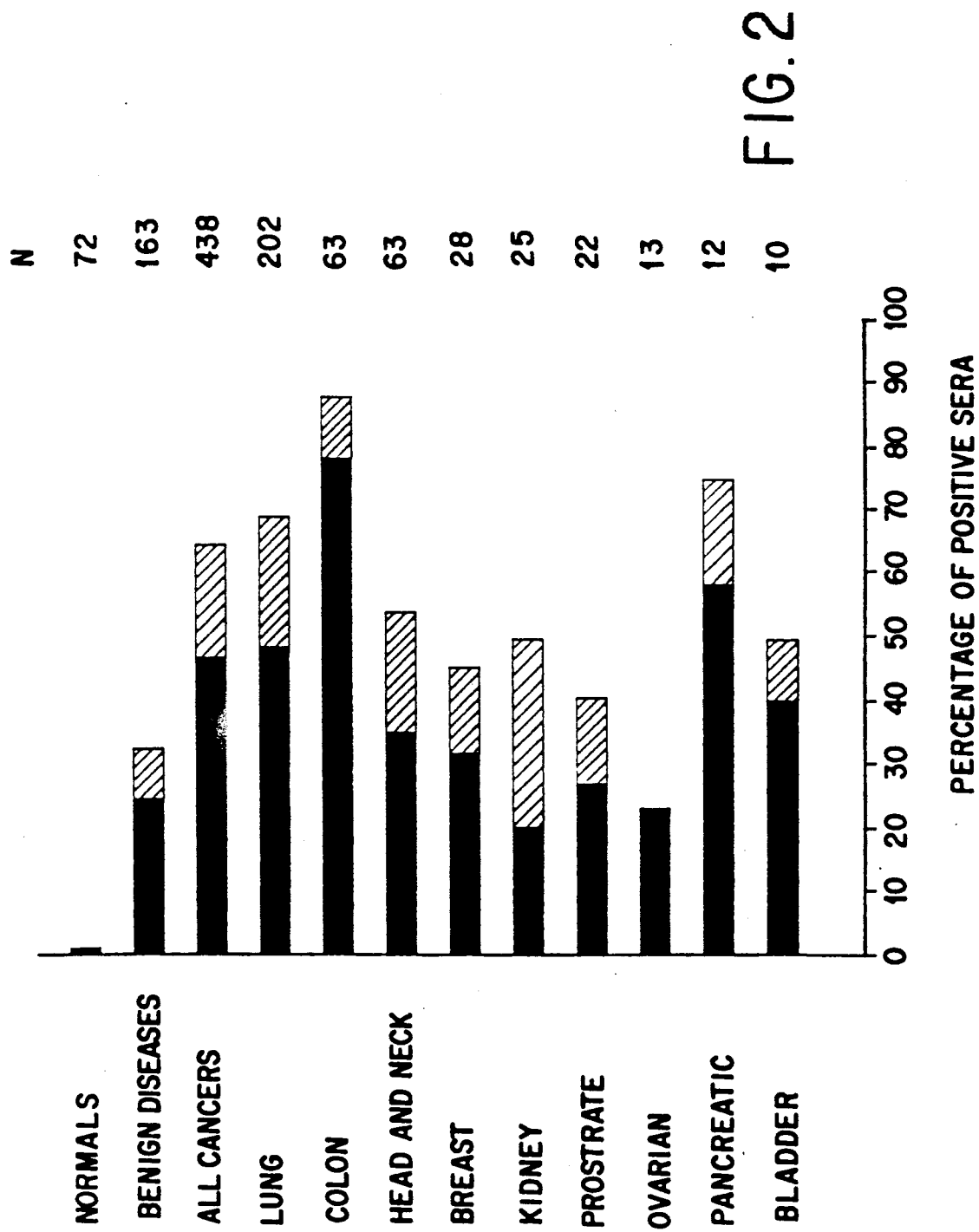
FIG. 2 shows the results of testing negative-CEA patient samples with the new assay.

All of the above specimens were also tested by carcinoembryonic antigen (CEA) immunoassay, the most commonly used assay for the monitoring of cancer patients. No correlation between serum CEA and the serum levels of altered $IgA_1$ was found. A correlation of $r=0.124$ was noted. Increased diagnostic sensitivity over CEA alone was obtained in all cancer types when CEA values and R values from the anti-IgA-PNA enzyme immunoassay were combined, except for ovarian cancer, as shown in FIG. 2. This occurred when some specimens from human cancer patients were CEA negative but tested as positive with the new assay. Therefore, it is believed that the present invention may have clinical utility as a supplementary test to the CEA assay.

EXAMPLE 2

Figure 3:
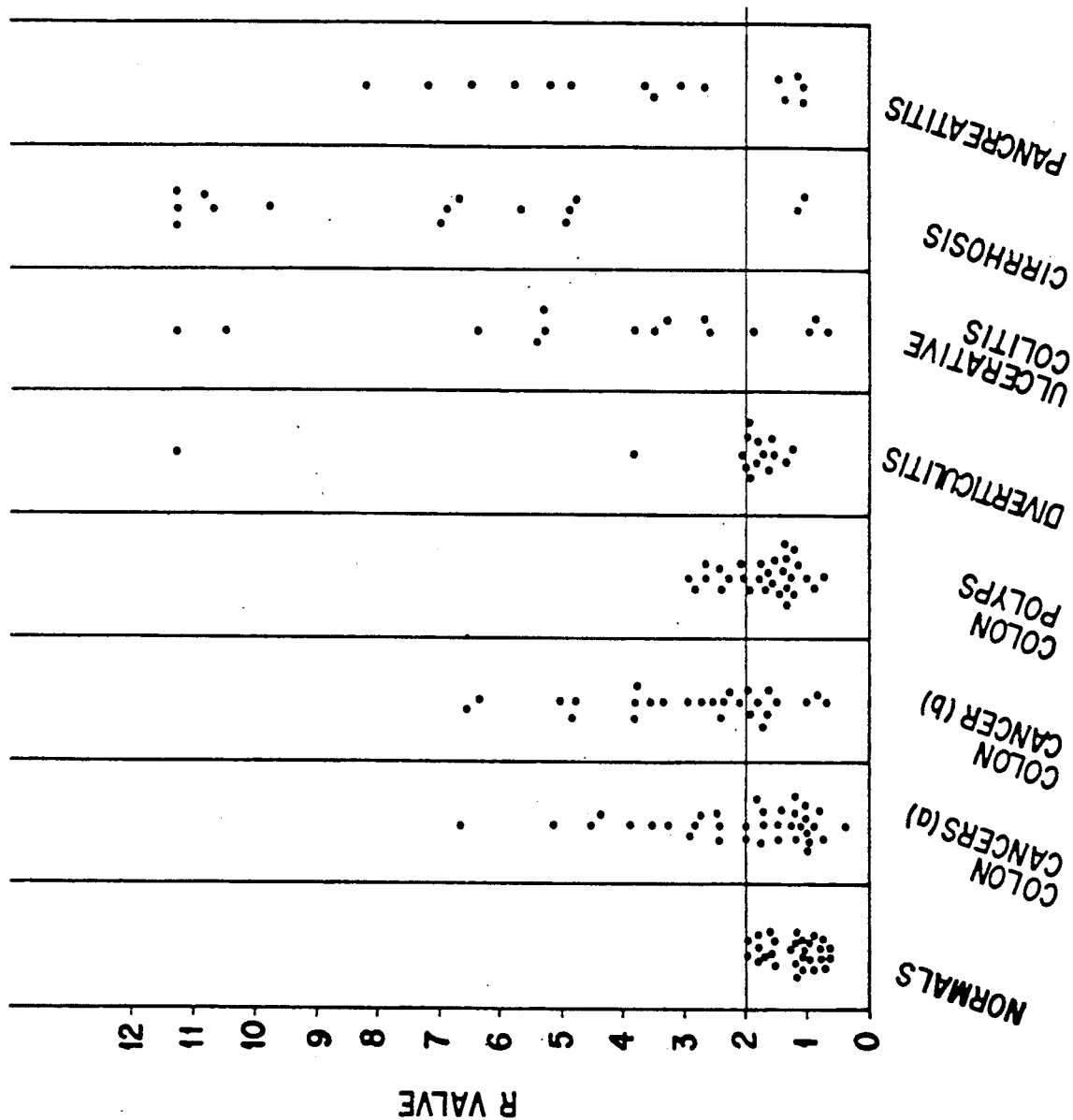
FIG. 3 shows results of testing 180 serum specimens from normal, non-cancerous and cancerous patients using a modified anti-IgA-peanut agglutinin enzyme immunoassay of Example 2.

FIG. 3 illustrates the results of testing using the method of Example 1 wherein the specimen diluent was modified to a composition of 0.1% bovine serum albumin, 0.02% Tween 20, 5 mM EDTA, 10 mM sodium phosphate, 150 mM NaCl, at pH 7.2.

The serum specimens tested by this assay were 29 normals, 36 colon cancer specimens with carcinoembryonic antigen assay (CEA) values of less than 5 ng/ml, 27 colon cancer specimens with CEA values greater than 5 ng/ml, 28 specimens from patients with colon polyps, 15 from patients with diverticulitis, 15 from patients with ulcerative colitis, 15 from patients with cirrhosis and 15 from patients with pancreatitis.

A cutoff R value of the normal mean plus 2 standard deviations was used. 0% of normals, 36% of colon cancer specimens with CEA values of less than 5 ng/ml, 59% of the colon cancer specimens with CEA values greater than 5 ng/ml, 25% of the colon polyp specimens, 13% of the diverticulitis specimens, 73% of the ulcerative colitis specimens, 87% of the cirrhosis specimens, and 67% of the specimens with pancreatitis were elevated above the cutoff value.

The results shown in FIG. 3 also demonstrate the use of this lectin assay as a supplemental assay to the widely used CEA assay for carcinomas. Values were elevated, to above the cutoff R value, for the premalignant conditions of colon polyps and ulcerative colitis and in 36% of the CEA negative colon cancer specimens (those with CEA levels of less than 5 ng/ml).

It is suggested that the CEA assay and the present assay can be used in an additive, or supplemental manner to jointly detect a greater number of premalignant and malignant conditions and for monitoring colon cancer patients for recurrence of disease.

The benign conditions that were detected were cirrhosis and pancreatitis. These results also suggest that the present invention may be useful in the diagnosis of these types of diseases.

EXAMPLE 3

This example describes an assay substantially the same as Example 1 the difference being the use of a radiolabeled lectin.

Anti-IgA PNA Radioimmunoassay

Polystyrene beads, 0.25 inch in diameter, are coated with rabbit antihuman IgA and are added to the wells of a reaction tray with 25 microliters of serum or standards, 200 microliters of assay diluent, as in Example 1. An assay blank is measured by substituting 25 microliters of assay diluent for the test sample. The trays are incubated for one hour at 37 degrees C. and are washed with distilled water and then incubated at room temperature for two hours with PNA labeled with $^{125}I$. The beads are incubated with the labeled lectin, washed again with distilled water and then transferred to tubes for counting bound $^{125}I$.

The anti-IgA-PNA enzyme immunoassay can be manufactured and distributed as an in-vitro diagnostic test kit. This kit, containing 0.25 inch polystyrene beads that are coated with anti-human IgA antibodies, a labeled lectin that has specificity for O-linked oligosaccharide on $IgA_1$, specimen dilution buffer and colostrum IgA standards.

We claim:

1. A method for determining the presence of amount of $IgA_1$ with O-linked oligosaccharides in a fluid sample comprising:
  a) contacting the sample with an anti-IgA antibody bound to a solid phase to form an anti-IgA/IgA solid phase complex;
  b) contacting said anti-IgA/IgA solid phase complex with a labeled lectin wherein said lectin binds to an O-linked oligosaccharide moiety of unmasked or exposed DGalBeta(1-3)DGalNAc oligosaccharide structures of $IgA_1$ thereby forming an anti-IgA/IgA$_1$/lectin solid phase complex when $IgA_1$ is present in the sample;

c) determining the presence or amount of label bound to said anti-IgA/IgA$_1$/lectin solid phase complex as a measure of the presence or amount of the IgA$_1$ with O-linked oligosaccharides in the sample.

2. The method of claim 1 wherein the label is selected from the group consisting of enzymes, radioisotopes and fluorescent molecules.

3. A method of claim 1 wherein the fluid sample is selected from the group consisting of blood, serum and plasma.

4. A method according to claim 1 wherein the lectin is selected from the group consisting of peanut agglutinin and Bauhinia purpurea alba agglutinin.

5. A method to determine the presence or amount of IgA$_1$ with O-linked oligosaccharide in a fluid sample comprising:
   a) absorbing an antibody specific for IgA immunoglobulin onto a solid phase;
   b) adding the sample to said antibody-coated solid phase and incubating to form an anti-IgA/IgA solid phase complex;
   c) washing said complex to remove any unreacted sample;
   d) adding an enzyme labeled lectin wherein said lectin binds to an O-linked oligosaccharide moiety of unmasked or exposed DGalBeta(1-3)DGalNAc oligosaccharide structures of IgA$_1$ thereby forming an anti-IgA/IgA$_1$/lectin solid phase complex;
   e) washing said anti-IgA/IgA$_1$/lectin solid phase complex;
   f) adding an enzyme substrate and incubating;
   g) quenching the enzyme reaction; and
   h) detecting the label as a measure of the presence or amount of the IgA$_1$ with O-linked oligosaccharide present in the sample.

6. The method of claim 5 wherein the enzyme label is selected from the group consisting of alkaline phosphatase, B-galactosidase, glucose oxidase and horseradish peroxidase.

7. The method of claim 5 wherein the enzyme label is horseradish peroxidase.

8. The method of claim 5 wherein the fluid sample is selected from the group consisting of blood, serum and plasma.

9. The method of claim 5 wherein the lectin is selected from the group consisting of peanut agglutinin and Gauhinia purpurea alba agglutinin.

10. A method to determine the presence or amount of IgA$_1$ with O-linked oligosaccharide in a fluid sample comprising:
    a) absorbing an antibody specific for IgA immunoglobulin onto a solid phase;
    b) adding the sample to said antibody-coated solid phase to form an anti-IgA/IgA solid phase complex;
    c) washing said complex to remove any unreacted sample;
    d) adding a radiolabeled lectin wherein said lectin binds to an O-linked oligosaccharide moiety of unmasked or exposed DGalBeta(1-3)DGalNAc oligosaccharide structure of IgA$_1$;
    e) incubating to form an anti-IgA/IgA$_1$/lectin solid phase complex when IgA$_1$ is present in the sample;
    f) washing said solid phase; and
    g) detecting said label as a measure of the presence or amount of the IgA$_1$ with O-linked oligosaccharide in the sample.

11. A method according to claim 10 wherein the fluid sample is selected from the group consisting of blood, serum and plasma.

12. A method according to claim 10 wherein the lectin is selected from the group consisting of peanut agglutinin and Bauhinia purpurea alba agglutinin.

13. A method for determining the presence or amount of IgA$_1$ with O-linked oligosaccharide in a carcinoembryonic antigen negative biologic fluid sample comprising:
    a) contacting the sample with an anti-IgA antibody bound to a solid phase to form an anti-IgA/IgA solid phase complex;
    b) contacting said anti-IgA/IgA solid phase complex with a labeled lectin wherein said lectin binds to an O-linked oligosaccharide moiety of unmasked or exposed DGalBeta(1-3)DGalNAc oligosaccharide structures of IgA$_1$ thereby forming an anti-IgA/IgA$_1$/lectin solid phase complex when IgA$_1$ is present in the sample; and
    c) determining the presence or amount of label bound to said anti-IgA/IgA$_1$/lectin solid phase complex as a measure of the presence or amount of the IgA$_1$ with O-linked oligosaccharide in the sample.

14. A kit for the testing of IgA$_1$ with O-linked oligosaccharide in a fluid sample, comprising:
    a first assay reagent comprising anti-human IgA antibodies immobilized upon a solid phase; and
    a second assay reagent comprising a labeled lectin wherein said lectin binds to an O-linked oligosaccharide moiety of unmasked or exposed DGalBeta(1-3)DGalNAc oligosaccharide structures of IgA$_1$.

15. The kit according to claim 14 further comprising a specimen dilution buffer and colostrum IgA standards.

* * * * *